United States Patent [19]

Jandacek et al.

[11] Patent Number: 5,017,398

[45] Date of Patent: * May 21, 1991

[54] IMPROVED MARGARINE COMPOSITIONS/CONTAINING SOLID SUCROSE POLYESTERS

[75] Inventors: Ronald J. Jandacek, Greenhills; James C. Letton, Forest Park, both of Ohio

[73] Assignee: The Procter & Gamble Company, Cincinnati, Ohio

[*] Notice: The portion of the term of this patent subsequent to Jan. 10, 2006 has been disclaimed.

[21] Appl. No.: 254,744

[22] Filed: Oct. 7, 1988

Related U.S. Application Data

[63] Continuation-in-part of Ser. No. 36,836, Apr. 10, 1987, Pat. No. 4,797,300.

[51] Int. Cl.$^5$ .............................................. A23D 7/00
[52] U.S. Cl. .................................... 426/603; 426/601; 426/602; 426/604; 426/611; 426/804; 536/119
[58] Field of Search ............... 426/602, 603, 604, 601, 426/804; 536/119

[56] References Cited

U.S. PATENT DOCUMENTS

| 2,999,023 | 9/1961 | Babayan et al. | 426/607 |
|---|---|---|---|
| 3,158,490 | 11/1964 | Baur et al. | 426/607 |
| 3,249,600 | 5/1966 | Nobile et al. | 260/234 |
| 3,344,796 | 10/1967 | Yamaji et al. | 131/267 |
| 3,600,186 | 8/1971 | Mattson et al. | 99/1 |
| 4,005,195 | 1/1977 | Jandacek | 424/312 |
| 4,241,054 | 12/1980 | Volpenhein | 536/119 |
| 4,611,055 | 9/1986 | Yamamoto et al. | 536/119 |
| 4,797,300 | 1/1989 | Jandacek et al. | 426/549 |

FOREIGN PATENT DOCUMENTS

| 227137 | 9/1985 | German Democratic Rep. |
|---|---|---|
| 228457 | 10/1985 | German Democratic Rep. |
| 52-27694 | 7/1977 | Japan . |
| 53-6219 | 3/1978 | Japan . |
| 53-6220 | 3/1978 | Japan . |
| 58-43744 | 3/1983 | Japan . |
| 58-56638 | 4/1983 | Japan . |
| 58-78531 | 5/1983 | Japan . |
| 58-165737 | 9/1983 | Japan . |
| 4926220 | 3/1984 | Japan . |
| 59-143550 | 8/1984 | Japan . |
| 59-156242 | 9/1984 | Japan . |
| 61-14123 | 4/1986 | Japan . |

Primary Examiner—Donald E. Czaja
Assistant Examiner—Evan Federman
Attorney, Agent, or Firm—Ronald L. Hemingway; Julius P. Filcik; Richard C. Witte

[57] ABSTRACT

Bread spread compositions (e.g., margarine) wherein the fat portion of the composition comprises a triglyceride oil or a non-digestible oil and a solid non-digestible sucrose polyester of a mixture of short chain and long chain saturated carboxylic acids, the molar ratio of short chain:long chain radicals being from about 4:4 to about 3:5 and the degree of esterification being from about 7 to about 8.

11 Claims, No Drawings

IMPROVED MARGARINE COMPOSITIONS/CONTAINING SOLID SUCROSE POLYESTERS

REFERENCE TO RELATED APPLICATION

This is a continuation-in-part of Application USSN 036,836, filed Apr. 10, 1987 U.S. Pat. No. 4,797,300 on Jan. 10, 1989.

FIELD OF THE INVENTION

The invention pertains to bread spread (e.g., margarine) composition wherein the fat portion of the composition comprises a triglyceride oil or a non-digestible oil, and a solid non-digestible sucrose fatty acid polyester which is capable of binding large amounts of oil within its crystal structure.

BACKGROUND OF THE INVENTION

The subject invention pertains to bread spread compositions (e.g. margarines). These compositions consist of an emulsion of an oil or fatty phase and an aqueous phase. The physical characteristics of a finished margarine such as solids content properties, spreadability, and ease of melting in the mouth, are to a large extent determined by the constituents which make up the fatty phase of the emulsion.

Margarine should melt readily in the mouth to avoid a sensation of "waxiness" or "stickiness" and to have a satisfactory flavor. This means there must be almost no fatty material in the solid state at or near body temperatures. On the other hand, at temperatures of use the margarine must be capable of being spread and this requires that some portion of the fatty material be in the solid state at that temperature, but not so much that the margarine is hard and difficult to spread and not so little that the margarine will "slump" or lose its shape.

In addition, it is usually preferred to produce a margarine product that duplicates or approaches the appearance of butter. In general, however, margarines are formulated to have better physical stability at high temperatures than butter and therefore can be stored in both refrigerated or non-refrigerated storage. In specific cases margarines can be produced deliberately different from butter in other characteristics, i.e. margarine can be made spreadable at refrigerated temperature. This is particularly true of the newer type so-called soft margarines which are packaged in tub form.

When some margarines are heated above about 70° F., part of their liquid oil content may start to seep or "oil-off" from the body of the margarine to the lower surfaces. This seepage increases with increase in temperature. If it becomes excessive, liquid oil can leak, soiling the container, In addition to making the package unsightly and oily to the touch, the oil is more susceptible to rancidity because of the greater exposure of the oil to the air. Further, since margarine contains an aqueous phase, bacterial or mold contamination can also occur.

It is generally recognized therefore that margarines must have sufficient heat resistance to resist oil-off under trade conditions.

The conventional way of improving heat resistance of a margarine is to increase the level of higher melting saturated (and trans unsaturated) solid fats in the fatty phase. However, such an increase, though improving the heat resistance of the margarine, results in an increased solids content and hence a significant loss in the eating quality or "melt in the mouth characteristics" of the margarine. It is also recognized that inclusion of saturated fats in the diet is undesirable from a coronary health standpoint. There is, therefore, a need for solid fat-like materials which can control oil seepage in margarines and, at the same time, maintain good eating quality. There is also a need to provide fat-like materials for margarine use which can replace saturated fats.

U.S. Pat. No. 3,600,186, Mattson et al. issued Aug. 17, 1971 discloses solid and liquid fatty acid esters of certain sugars and sugar alcohols which have the physical properties of natural fats and oils but are nondigestible. The reference teaches that these compounds can be used as total or partial substitutes for natural fats in foods, including margarine and dairy products.

European Patent Application 233,856, Bernhardt, published Aug. 26, 1987 discloses compositions comprising sucrose polyesters having specified physical characteristics and triglycerides. Margarine is one of the types of compositions mentioned.

SUMMARY OF THE INVENTION

The invention is directed to bread spread compositions of the margarine type in which the oil phase comprises a liquid triglyceride oil or nondigestible oil, and a solid nondigestible fat which is a fatty acid ester of sucrose wherein the fatty acid groups consist essentially of short chain fatty acid radicals containing from 2 to 10 carbon atoms and long chain fatty acid radicals containing from 20 to 24 carbon atoms in a molar ratio of short chain:long chain radicals of 4:4 to 3:5, the said esters having a degree of esterification of about 7 to 8.

DETAILED DESCRIPTION OF THE INVENTION

The present invention is directed to bread spread compositions of the margarine type. As defined in the United States Federal Food Drug and Cosmetic Act, margarine must contain at least 80% fat. Although margarine per se is a preferred bread spread composition of the present invention, the compositions of the present invention can contain as low as about 50% fat, i.e. the fatty phase can be as low as 50% by weight of the composition. For convenience, compositions of the present invention will be referred to herein simply as "spreads."

The spreads of the present invention comprise
 (a) from about 50% to about 90% of a mixture consisting essentially of:
  (i) an edible oil selected from triglyceride oils and non-digestible oils, or mixtures thereof, said oil having a solid fat content of 1% or less at 50° F. and 0% at 70° F.;
  (ii) a solid fatty acid ester of sucrose, the fatty acid groups consisting essentially of saturated straight chain short chain fatty acid radicals containing from 2 to 10 carbon atoms and saturated straight chain long chain fatty acid radicals containing from 20 to 24 carbon atoms, the molar ratio of short chain to long chain radicals being from about 4:4 to 3:5 and the degree of esterification being from about 7 to about 8;
  the weight ratio of (i) to (ii) being from about 3:1 to about 9:1;
 (b) from about 0.01% to about 15% of an emulsifier;
 (c) from 0% to about 5% milk solids;
 (d) from 0% to about 3.5% salt; and
 (e) the balance, water.

All percentages and ratios herein are "by weight", unless specified otherwise.

Solid Sucrose Polyester

The fatty acid esters of sucrose defined in (a)(ii) above are solid (at temperatures up to about 40° C.) nondigestible fat-like materials which have been found to have high binding capacity for oils. They are substantially completely esterified polyesters of sucrose wherein the esterifying acid groups are a mixture of short chain and long chain saturated straight chain fatty acid radicals. The short chain acid radicals contain from 2 to 10, preferably 6 to 10, and most preferably 8 to 10 carbon atoms and the long chain acid radicals contain from 20 to 24 (preferably 22) carbon atoms.

The molar ratio of short chain to long chain acid radicals in the polyester molecule is from about 4:4 to about 3:5 and the average degree of esterification is from about 7 to about 8, i.e., from about 7 to all 8 of the hydroxyl groups of sucrose are esterified.

Examples of short chain fatty acid radicals for use in the solid sucrose polyester (SPE) compounds herein are acetate, butyrate, hexanoate (caproate), octanoate (caprylate) and decanoate (caprate). Examples of suitable long chain fatty acid radicals are eicosanoate (arachidoate), docosanoate (behenate), and tetracosanoate (lignocerate). The preferred short chain fatty acid radical is caprylate and the preferred long chain fatty acid radical is behenate. The preferred ratio of short chain fatty acid to long chain fatty acid is 3:5 and it is preferred that all of the hydroxyl groups of sucrose be esterified, i.e., that the compound be the octaester. The most preferred solid SPE compound for use in compositions of the invention is sucrose tricaprylate pentabehenate.

The solid SPE compounds herein can be made according to prior known methods for preparing polyesters of sucrose. One such method is by reacting the acid chlorides of the fatty acids with sucrose. In this method a mixture of the long and short chain acid chlorides can be reacted in one step with sucrose, or the long and short chain acid chlorides can be reacted sequentially with sucrose. Another preparation method is by the process of reacting methyl esters of the fatty acids with sucrose in the presence of a fatty acid soap and a basic catalyst such as potassium carbonate. See, for example, U.S. Pat. No. 3,963,699, Rizzi et al., issued June 15, 1976; U.S. Pat. No. 4,518,772, Volpenhein, issued May 21, 1985; and U.S. Pat. No. 4,517,360, Volpenhein, issued May 14, 1985, all incorporated herein by reference. When using the methyl ester route for preparing the compounds herein, the octaester of the short chain fatty acid is prepared first, then this product is partially interesterified with the methyl ester of the long chain fatty acid in order to obtain the sucrose ester of mixed short chain/long chain fatty acids.

The solid SPE compounds of the present invention are all solids at temperatures below about 40° C. They have the ability to trap large amounts of oil within their crystal structure, and as a consequence, can be blended in relatively small amounts with liquid oils to provide a fat composition having suitable properties for use as the fatty phase in a spread.

Some of the solid SPE compounds of the present invention exhibit a beta prime-like crystal structure which is characteristic of triglycerides, however, not all of the solid SPE compounds of the invention exhibit this structure and it is not a required characteristic for the said compounds to be useful in the invention.

A listing of representative solid sucrose polyesters for use in compositions of the present invention is shown in the following table.

| | Short Chain Acid* | Long Chain Acid* | Ratio of Short:Long Chain** | Average Degree of Esterification | Melting Point °C. | Hydroxyl Value |
| --- | --- | --- | --- | --- | --- | --- |
| 1 | $C_4$ | $C_{22}$ | 4:4 | 7.99 | 49 | 0.22 |
| 2 | $C_6$ | $C_{22}$ | 4:4 | 7.97 | 44 | 0.65 |
| 3 | $C_8$ | $C_{22}$ | 4:4 | 7.88 | 48 | 3.1 |
| 4 | $C_{10}$ | $C_{22}$ | 4:4 | 7.87 | 47 | 3.2 |
| 5 | $C_8$ | $C_{24}$ | 4:4 | 7.81 | 52 | 5.5 |
| 6 | $C_2$ | $C_{22}$ | 4:4 | 7.87 | 58 | 4.2 |

*Straight chain saturated monocarboxylic acids.
**Ratio of moles of short chain:long chain acid chlorides used in the reaction to prepare the desired products.
Note: Compounds 1 through 5 have a beta prime-like crystal structure.

It is known that nondigestible oils which are liquids at temperatures below body temperature can cause anal leakage when ingested, depending upon the amount ingested. See U.S. Pat. No. 4,005,195, issued Jan. 25, 1977, incorporated by reference herein. The said patent discloses numerous materials which can be used as anti-anal leakage agents (AAL's) to inhibit such leakage. Among the materials disclosed for this purpose are nondigestible fatty acid esters of polyols (e.g., sucrose polyesters) which are solids above body temperature. Because of their high oil binding capacity, the short chain:long chain solid sucrose polyesters of the present invention are especially effective AAL agents for liquid non-digestible oils in the spread compositions of the present invention in which a nondigestible oil is used as the edible oil component.

Edible Oil

The edible oils used in the compositions of the invention can be conventional digestible triglyceride oils or they can be nondigestible oils. The oil should have a complete melting point of 70° F. or less, i.e., its SFC (Solid Fat Content) at 70° F. should be 0%. Preferably, the oil should have an SFC of about 1% or less at 50° F. (10° C.) and 0% at 70° F. (21° C.). SFC is a commonly used measurement in the fats and oils industry. One method of doing the measurement is by pulsed nuclear magnetic resonance (PNMR). The fat material sample is heated to a temperature at which it is completely melted and held there for 0.5 hours. The melted sample is then tempered at a temperature of 40° F. (4.4° C.) for at least 72 hours. After tempering, the SFC value of the fat material at any desired temperature is determined by PNMR. The method for determining SFC values of a fat by PNMR is described in Madison and Hill, *J. Amer. Oil Chem. Soc.*, Vol. 55 (1978), pp. 328-31 (herein incorporated by reference).

The digestible oils can be derived from animal, vegetable or marine sources, and include naturally occurring oils such as cottonseed oil, soybean oil, sunflower oil, corn oil, peanut oil and mixtures thereof.

Examples of nondigestible edible oils are liquid polyesters of sugars and sugar alcohols (U.S. Pat. No. 4,005,195, Jandacek, issued Jan. 25, 1977); liquid esters of tricarballylic acids (U.S. Pat. No. 4,508,746, Hamm, issued Apr. 2, 1985); liquid diesters of dicarboxylic acids such as malonic and succinic acid (U.S. Pat. No. 4,582,927, Fulcher, issued Apr. 15, 1986); liquid triglycerides of alpha-branched chain carboxylic acids (U.S. Pat. No. 3,579,548, Whyte, issued May 18, 1971); ethers and ether esters containing the neopentyl moiety (U.S. Pat. No. 2,962,419, Minich, issued Nov. 29, 1960); fatty polyethers or polyesters of polyglycerol (U.S. Pat. No 3,932,532, Hunter et al., issued Jan. 13, 1976); all incorporated herein by reference.

The preferred nondigestible oils are polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms. Examples of these are liquid fatty acid esters of sucrose (e.g., sucrose octaoleate) and liquid fatty acid esters of sorbitol (e.g., sorbitol hexaoleate). Other examples may be found in U.S. Pat. No. 3,600,186, Mattson, issued Aug. 17, 1971, incorporated herein by reference.

Mixtures of digestible and nondigestible oils can be used. The weight ratio of edible oil to solid fatty acid ester of sucrose in the composition herein should be from about 3:1 to about 9:1, preferably from about 5:1 to about 9:1, and most preferably from about 3:1 to about 5:1.

Emulsifier

An emulsifier is a component of the oil phase of the compositions herein. Examples of emulsifiers useful herein are mono- and diglycerides, lecithin and polyoxyethylene sorbitan monoesters such as Tween ® 60 and Tween ® 80. The emulsifiers are used at levels of from about 0.01% to about 15%, preferably from about 0.1% to about 0.5%.

The oil phase can also include oil soluble flavorants and colorants.

Other Components

Usually milk solids will be present in an amount to provide up to about 5% (preferably about 0.5% to about 5%, most preferably about 1% to about 3%) milk solids in the spread composition. When milk solids are used, the water in the aqueous phase should be distilled or deionized. For a non-browning spread, the milk solids or the reducing sugars in the milk solids are eliminated.

Usually salt will also be present at a level of up to about 3.5% (preferably about 0.5% to 3 5%, most preferably about 1% to about 2.5%) of the spread composition.

Other materials such as preservatives, flavorants, colorants, etc. can be included in the spread compositions herein.

Water is an essential component of the spreads herein. Water typically comprises from about 1% to about 45% (more typically about 5% to about 45%) of the composition.

Manufacture

Spreads of the present invention can be manufactured by conventional procedures used in the manufacture of margarine. For example, the aqueous phase ingredients (water, milk solids, salt, water soluble flavors, preservatives, etc.) are dispersed in the oil phase (melted mixture of oil and solid SPE, emulsifiers, and oil soluble color and flavor) and the mixture is processed through an apparatus known as a Votator. A unit of the Votator is a scraped wall heat exchanger. Besides chilling the emulsified fat, the high local pressure and shearing action of the A unit induces fast nucleation and crystallization of solids during the short residence time (0.5 to 60 seconds). The chilled emulsion is then sent to a crystallizer, known as the B unit of the Votator. Static B units, in the form of a hollow tube or resting tube normally provide firm stick-type margarines. Working B units, in the form of picker boxes, serve to break up large crystals and lead to softer margarines. See Haighton, "Blending, Chilling, and Tempering of Margarines and Shortenings", J. Am. Oil Chemists Soc., Vol 53 (June, 1976), pp. 397–399; Wiedermann, "Margarine and Margarine Oil, Formulation and Control", J. Am. Oil Chemists Soc., Vol. 55 (December, 1978), pp. 823–829, and U.S. Pat. No. 4,568,556, McCoy, issued Feb. 4, 1986, all incorporated by reference herein.

U.S. Pat. Nos. 4,217,372 and 4,087,565 to Ebskamp, issued Aug. 12, 1980 and May 2, 1978, respectively, disclose methods for improving the physical structure of fats in a margarine wherein the margarines are cooled, then mechanically worked and cooled again to a temperature lower than the first cooling. See also Chikany, "Crystallization Process of Fats and Their Role in Margarine Production. Part II", Olaj, Szappan, Kozmetika, 13:9–13 (1982)

The present invention will be illustrated by the following examples.

EXAMPLE I

Preparation of Tetrabehenyl Tetracaprylyl Sucrose (Acid Chloride Route)

| Chemicals: | Mol. Wt. | Wt. (g) | Moles | Mole Ratio |
|---|---|---|---|---|
| A. Reaction | | | | |
| 1. Sucrose | 342.3 | 7 | 0.0204 | 1 |
| 2. Behenyl Chloride (Docosanoyl Chloride) | 358.6 | 30 | 0.0836 | 4.09 |
| 3. Caprylyl Chloride (Octanoyl Chloride) | 162 | 15 | 0.0925 | 4.53 |
| B. Solvents | | | | |
| 1. Pyridine | | | | |
| 2. Dimethylformamide | | | | |
| 3. Dichloromethane | | | | |
| 4. Methanol | | | | |

Procedure

Seven grams of sucrose (anhydrous) were dissolved by warming in a mixture of 150 ml pyridine and 75 ml of dimethylformamide (DMF). Both solvents had been dried over 4A molecular sieves.

Thirty grams of the acid chloride of behenic ($C_{22}$) acid were dissolved in 100 ml of dichloromethane and the acid chloride solution added dropwise to the sucrose solution. The reaction temperature was held at 32° C. by use of a cold water bath. Addition time was 30 minutes.

After addition of the $C_{22}$ acid chloride, the reaction mixture was warmed to 40° C., removed from the water bath and allowed to stir at ambient temperature for four additional hours.

After four hours of reaction time, 15 grams of caprylyl chloride in 50 ml of dichloromethane were added. Addition time was 30 minutes and the reaction temperature was maintained at 30°–35° C. After addition of the caprylyl chloride, the reaction mixture was allowed to stir overnight.

After stirring overnight, the reaction mixture was diluted with 30 ml of methanol to convert excess acid chlorides to their methyl esters. The reaction mixture was then diluted with 300 ml of dichloromethane and combined in a separatory funnel with 300 ml of a dilute salt (NaCl) solution. The mixture was shaken then allowed to separate.

The organic (dichloromethane) layer was washed a second time with a dilute salt solution followed by washing with dilute HCl (to remove residual pyridine), then with water until the last wash was neutral to pH paper.

The dichloromethane solution was dried over anhydrous sodium sulfate then stripped under vacuum with heating to a liquid residue. The product solidified on standing. The solid product was melted in a hot water bath then extracted three times with methanol (the methanol layers were removed by decantation). The reaction product was stripped again under vacuum and the residue dissolved in 80 ml of dichloromethane. The solution was stirred and 80 ml of methanol were slowly added to induce crystallization. The mixture was again vacuum distilled to displace the dichloromethane with additional methanol added during distillation. A white precipitate (crystalline) formed and the suspension was cooled in a water bath then filtered to give 40.5 grams of dried product.

Yield—93% of theoretical

Analytical

Hydroxyl value—3.1
2. Average degree of esterification 7.88 (calculated from hydroxyl value as an approximation)
3. Estimated % octaester—90.6

EXAMPLE II

Preparation of TetrabehenYl Tetracaprylyl Sucrose (Methyl Ester Route)

An alternative method for preparation of $C_8$–$C_{22}$ sucrose polyesters is by a modification of the process described in U.S. Pat. Nos. 4,518,772, supra, and 4,517,360, supra. Sucrose is reacted with methyl caprylate in the presence of a potassium soap and a basic catalyst such as $K_2CO_3$ to form sucrose octacaprylate. The octacaprylate is then reacted with methyl behenate in the presence of sodium methoxide for an interesterification to the $C_8$–$C_{22}$ product of interest.

| Chemicals: | Mol. Wt. | Wt. (g) | Moles | Mole Ratio |
|---|---|---|---|---|
| A. Reaction | | | | |
| 1. Sucrose | 342.30 | 300.00 | 0.876 | 1.000 |
| 2. Potassium Behenate | 378.60 | 124.10 | 0.328 | 0.375 |
| 3. Methyl Caprylate | 158.24 | 1663.40 | 10.512 | 12.000 |
| 4. Methyl Behenate | 354.60 | 2174.40 | 6.132 | 7.000 |
| 5. Potassium Carbonate | 138.21 | 12.107 | 0.0876 | 0.100 |
| 6. Sodium Methoxide | 54.00 | (½% by wt. of mixture) | | |
| B. Solvents | | | | |
| 1. Methanol | | | | |
| 2. Hexane | | | | |

Procedure

Step A—Preparation of Potassium Behenate

Methyl behenate (0.375 moles/mole of sucrose to be used in Step B) is saponified by stirring at reflux in methanol containing an equivalent amount of KOH. The reaction is stirred with heating until all methyl ester has been converted to soap as indicated by infrared analysis. The soap solution is used, as is in the next reaction step.

Step B—Preparation of Sucrose Octacaprylate

Methyl caprylate (12 moles/mole of sucrose) is added directly to the potassium behenate-methyl alcohol solution from Step A above. The mixture is stripped under vacuum to remove the methanol. Sucrose and potassium carbonate are then added to the soap-methyl caprylate mixture and the reaction mixture heated to 135° C. and placed under a partial vacuum.

The reaction is allowed to proceed until the sucrose is converted to its octacaprylate. The endpoint is determined by liquid or super critical fluid chromatography.

The reaction mixture is cooled to 95° C. and 7% $H_2O$ is added to form the hydrate of the soap.

The soap separates as a sludge and is removed by centrifugation, filtration and/or decantation. The oil layer (sucrose octacaprylate/methyl ester layer) is washed several times with hot water, separated and the residual water removed by $N_2$ sparging at 110° C.

The crude octacaprylate is then decolorized with a mixture of filtrol and celite and the bleaching earths removed by vacuum filtration. The excess methyl esters are removed by distillation at 130° C. and 1 mm Hg.

Step C—Preparation of $C_8$–$C_{22}$ Sucrose Polyesters

Sucrose octacaprylate (from Step B above) and 7 moles of methyl behenate are combined with sodium methoxide in a reactor. While stirring, the temperature is raised to 120° C. and the reactor placed under vacuum.

The methyl caprylate formed during interesterification is distilled from the reaction mixture and collected. The reaction is continued until 4–5 moles of methyl caprylate are collected (the ratio of $C_8$–$C_{22}$ on the sucrose may be adjusted by the amount of methyl caprylate removed).

The reaction mixture is then cooled to 90° C. and neutralized with glacial acetic acid.

The product is diluted with hexane and the hexane solution washed several times with hot water.

The water washes are separated and the hexane, along with any residual water, is removed via $N_2$ sparging at 110° C. The product is then rediluted with hexane and is decolorized with a mixture of charcoal and filtrol.

The charcoal/filtrol is removed by vacuum filtration and the solvent removed by vacuum distillation. Excess and/or residual methyl esters are removed by thin film evaporation and the product crystallized from a hexane/methanol solution.

(Steam stripping at 210° C. and 1 mm Hg is an optional final step.)

EXAMPLE III

A spread composition of the present invention is made according to the following formula:

| Ingredient | % By Weight |
|---|---|
| Sucrose octaoleate | 68.0 |
| Tetrabehenyl tetracaprylyl sucrose | 12.0 |
| Milk solids | 2.0 |
| Salt | 2.0 |
| Fatty monoglyceride | 15.0 |
| Water | 1.0 |
| Total | 100.0 |

EXAMPLE IV

Preparation of Pentabehenyl Tricaprylyl Sucrose (Acid Chloride Route)

| Chemicals: | Mol. Wt. | Wt. (g) | Moles | Mole Ratio |
|---|---|---|---|---|
| A. Reaction | | | | |
| 1. Sucrose | 342.3 | 8 | 0.0233 | 1 |
| 2. Behenyl Chloride | 358 | 41.71 | 0.1165 | 5 |
| 3. Caprylyl Chloride | 162 | 11.32 | 0.0699 | 3 |
| B. Solvents | | | | |
| 1. Pyridine | | | | |
| 2. Dimethylformamide | | | | |
| 3. Dichloromethane | | | | |
| 4. Methanol | | | | |

C. Procedure

While stirring, 8 g. anhydrous sucrose are dissolved in a mixture of 150 g pyridine and 75 ml dimethyl formamide. Dissolution is accomplished by heating in a hot water bath at about 55° C. After the sucrose is completely dissolved, the solution is cooled to 45° C. and 41.71 g. behenyl chloride in 125 ml dichloromethane are added slowly over a period of 1 hour. The reaction mixture is warmed to 52° C. and then allowed to stir at ambient temperature for 3 hours.

The reaction mixture is then warmed to 50° C. and 11.32 g (+3.5 g. excess) of caprylyl chloride in 50 ml dichloromethane are added over one-half hour and the reaction mixture is left stirring for about 16 hours.

The reaction mixture is then warmed to 55° C. and held at this temperature for 1 hour, then allowed to cool to 40° C. while stirring for an additional hour. Methanol is then added to react with any excess acid chloride, and the total reaction mixture is transferred to a distilling flask to remove the solvent under vacuum.

The distillation residue is dissolved in 500 ml of dichloromethane and washed twice with water and then with hydrochloric acid, followed by additional water washing until neutral.

The neutral dichloromethane solution is then stirred over magnesium sulfate (drying agent) for about 16 hours, and is then filtered and vacuum stripped.

The residue is dissolved in dichloromethane and the solution poured into 1 liter of methanol (with stirring) for crystallization. The crystalline product is then isolated by filtration.

EXAMPLE V

A spread composition of the following formula is prepared.

| Ingredient | % By Weight |
|---|---|
| Canola oil* | 67.5 |
| Pentabehenyltricaprylyl sucrose | 11.8 |
| Salt | 1.3 |
| Non-fat milk solids | 1.5 |
| Myverol emulsifier** | 0.6 |
| Lecithin | 0.3 |
| Butter flavor | 0.4 |
| Beta carotene | 0.02 |
| Water | 16.8 |
| Total | 100.22 |

*Low-erucic Acid rapeseed oil in which the fatty acid radicals of the triglyceride are in approximately the following percentages: oleic 62%; linoleic 22%; -linolenic 10%; saturates 5.5%; other (primarily erucic) 0.5%.
**Fatty monoglyceride emulsifiers from Eastman Chemical Products, Inc.

134.99 g canola oil is placed in a glass beaker with a stir bar and heated to 60° C. 23.69 g of tetrabehenyl tetracaprylyl sucrose is then added to the oil and stirred until melted. The remaining ingredients are then added in the following order while maintaining the temperature of about 60° C. 2.63 g salt; 3.05 g non-fat milk solid, 1.21 g Myverol emulsifier; 0.6 g lecithin; 33.68 g water; 0.8 g butter flavor; and 0.036 g beta carotene. Mixing is continued for 10 minutes at 60° C. The beaker is then removed from the heat and cooled while mixing is continued for about 10 minutes. The sample may be homogenized with a hand-operated homogenizer prior to refrigeration. The composition is then refrigerated for about 24 hours at 4° C. The composition has a satisfactory tub margarine texture and does not separate into an oil and solid phase when allowed to stand. It has good mouthfeel and does not leave a waxy residue in the mouth.

What is claimed is:

1. A bread spread comprising:
   (a) from about 50% to about 90% of a mixture consisting essentially of:
      (i) an edible oil selected from the group consisting of triglyceride oils and non-digestible oils, and mixtures thereof, said oil having a solid fat content of 1% or less at 50° F. and 0% at 70° F.;
      (ii) a solid fatty acid ester of sucrose, the fatty-acid groups consisting essentially of saturated straight chain short chain fatty acid radicals containing from 2 to 10 carbon atoms and saturated straight chain long chain fatty acid radicals containing from 20 to 24 carbon atoms, the molar ratio of short chain to long chain radicals being from about 4:4 to 3:5 and the degree of esterification being from about 7 to about 8;
   the weight ratio of (i) to (ii) being from about 3:1 to about 9:1;
   (b) from about 0.01% to about 10% of an emulsifier;
   (c) from about 0.5% to about 5% milk solids;
   (d) from about 0.5% to about 3.5% salt; and
   (e) the balance, water.

2. The composition of claim 1 wherein the edible oil is a triglyceride.

3. The composition of claim 2 wherein the ratio of Component (a)(i) to Component (a)(ii) is from about to about 9:1.

4. The composition of claim 3 wherein the short chain acid radicals of the solid polyester of sucrose contain from 6 to 10 carbon atoms and wherein the long chain acid radical is behenate.

5. The composition of claim 4 wherein the short chain acid radical is caprylate and the long chain acid radical is behenate.

6. The composition of claim 1 wherein the edible oil is a non-digestible oil.

7. The composition of claim 6 wherein the ratio of Component (a)(i) to Component (a)(ii) is from about 5:1 to about 9:1.

8. The composition of claim 7 wherein the nondigestible edible oil is a polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms.

9. The composition of claim 8 wherein the polyol is sucrose.

10. The composition of any one of claims 6, 7, 8 or 9 wherein the short chain acid radicals of the solid polyesters of sucrose contain from 6 to 10 carbon atoms.

11. The composition of any of claims 6, 7, 8 or 9 wherein the short chain acid radical is caprylate and the long chain acid radical is behenate.

* * * * *